United States Patent
Schares et al.

(10) Patent No.: US 10,240,211 B2
(45) Date of Patent: Mar. 26, 2019

(54) SYSTEMS AND METHODS FOR PERICARP GENOTYPING

(71) Applicant: PIONEER HI BRED INTERNATIONAL INC, Johnston, IA (US)

(72) Inventors: Justin Schares, Ames, IA (US); Yue Yun, Johnston, IA (US); Chengfeng Zhao, Ankeny, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 202 days.

(21) Appl. No.: 14/473,074

(22) Filed: Aug. 29, 2014

(65) Prior Publication Data

US 2016/0060712 A1  Mar. 3, 2016

(51) Int. Cl.
*C12Q 1/6806* (2018.01)
*C12Q 1/6895* (2018.01)

(52) U.S. Cl.
CPC ......... *C12Q 1/6895* (2013.01); *C12Q 1/6806* (2013.01); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 9,078,427 B1 | 7/2015 | Arnold et al. | |
| 9,416,394 B2 | 8/2016 | Rapier et al. | |
| 10,011,828 B2 | 7/2018 | Hannappel | |
| 2004/0043117 A1 | 3/2004 | Cope et al. | |
| 2009/0011411 A1* | 1/2009 | Hino | C12Q 1/6895 435/6.15 |
| 2013/0210006 A1* | 8/2013 | Rapier | C12Q 1/24 435/6.11 |

FOREIGN PATENT DOCUMENTS

| WO | 2011/119763 A1 | 9/2011 |
|---|---|---|
| WO | 2013/119962 A1 | 8/2013 |
| WO | 2013/182646 A1 | 12/2013 |

OTHER PUBLICATIONS

Manen (BMC Plant Biology 2005 vol. 5 No. 23 pp. 1-9).*
Somers (Methods in Molecular Biology, Plant Genomics vol. 513 pp. 19-39 Feb. 3, 2009).*
Griffiths (Journal of Experimental Botany vol. 50 No. 335 pp. 793-798 Jun. 1999).*
Thonur (BMC Veterinary Research 2012 vol. 8:37 pp. 1-9).*
Meru et al. Geneticts and Molecular Research, 2013, 12(1): 702-709.*
DNeasy Plant Handbook, Oct. 1, 2012—Anonymous, CP055216421.
Allen Griffiths et al., Ethylene and developmental signals regulate expression of lipoxygenase genes during tomato fruit ripening, Journal of Experimental Botany, Jun. 1999, pp. 793-798, vol. 50, No. 335.
Delphine Grivet et al., A novel approach to an old problem: tracking dispersed seeds, Molecular Ecology, 2005, pp. 3585- 3595, vol. 14.
Jean-Francois Manen et al., A fully automatable enzymatic methods for DNA extraction from plant tissues, BMC Plant Biology, 2005, pp. 1-9, vol. 5 No. 23.
G. Meru et al., A non-destructive genotyping system from a single seed for marker-assisted selection in watermelon, Genetics and Molecular Research, 2013, pp. 702-709, vol. 12(1).
Peter E. Smouse et al. Using Seedling and Pericarp Tissues to Determine Maternal Parentage of Dispersed Valley Oak Recruits, Journal of Heredity, 2012, pp. 250-259, vol. 103(2).
Daryl J Somers et al., New Technologies for Ultra-High Throughput Genotyping in Plants, Methods in Molecular Biology, Plant Genomics, 2009, pp. 19-39, vol. 513.
N Sreenivasulu et al., Identification of genes specifically expressed in maternal and filial tissues of barley caryopses: a cDNA array analysis, Mol. Genet Genomics, 2002, pp. 758-767, vol. 266.
Leenadevi Thonur et al., One-step multiplex real time RT-PCR for the detection of bovine respiratory syncytial virus, bovine herpesvirus 1 and bovine parainfluenza virus 3, BMC Veterinary Research, 2012, pp. 1-9, vol. 8:37.
Birgit Ziegenhagen et al., Molecular identification if individual oak and fir trees from maternal tissues of their fruits or seeds, Trees, 2003, pp. 345-350, vol. 17:345.
International Search Report—PCT/US2015/034134—dated Oct. 7, 2015.

* cited by examiner

*Primary Examiner* — Sarae L Bausch

(57) ABSTRACT

The invention includes methods for obtaining samples of maternal tissue from seeds, obtaining genetic material from the maternal seed tissue, and performing a molecular analysis on the genetic material from the maternal seed tissue to determine maternal lineage of a single seed. The invention also includes methods for establishing a consensus maternal genotype from maternal seed tissues obtained from multiple seeds as well as methods for determining paternal lineage.

3 Claims, 4 Drawing Sheets c)

b)

a)

SYSTEMS AND METHODS FOR PERICARP GENOTYPING

BACKGROUND OF THE INVENTION

Figure 1:
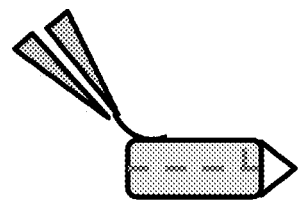
Figure 1:
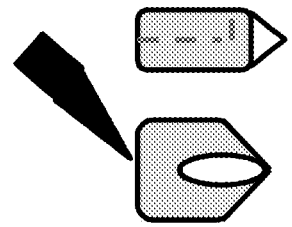
Figure 1:
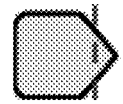

A seed is an embryonic plant enclosed in a protective outer covering called the seed coat. In monocots, the seed coat is fused with the pericarp, which is composed of multiple layers of cells and contains genetic code from the maternal parent only. As such, pericarp tissue can be used to identify the maternal lineage of a seed. Paternal lineage can be further derived from the pericarp genotype in combination with the seed (embryo or endosperm) genotype, which contains the genetic information from both maternal and paternal background. Determining lineage is important for germplasm security to ensure that proprietary parental lines remain proprietary.

Tissues or other adhering structures connect the pericarp to the interior part of the seed, mainly endospermic tissue. This, coupled with the relatively small size of most seeds, can make separation and removal of pericarp difficult, or at least time consuming and laborious. Molecular analysis of impure pericarp tissue contaminated with interior seed tissue (e.g. endosperm), which carries both maternal and paternal genetic information, leads to ambiguous genetic identification of the maternal lineage. Therefore, an efficient pericarp removal and purifying method is required prior to molecular analysis.

Pericarp removal processes have been developed and used in the art for both food processing and pericarp molecular analysis. Some pericarp removal methods involve soaking corn kernels in a chemical solution (e.g. sodium hydroxide (NaOH) and/or hydrogen peroxide ($H_2O_2$)) for a relatively long period of time (e.g. hours). Such chemical soaking has been found to substantially loosen pericarp such that an automated method of separation can be used to separate the loosened pericarp from the endosperm. The methods allow batches of a substantial number of kernels to be processed. However, such processes require chemicals, as well as costs and handling associated with them. Most importantly, the chemicals used combined with the significant amount of time of soaking may damage or otherwise affect the DNA in the pericarp.

To avoid damage to DNA when separating pericarp from the remainder of the kernel for molecular analysis, current conventional methodologies have stayed away from chemical steeping. Instead, current methods involve trying to loosen the pericarp by soaking the kernels overnight in distilled water instead of chemicals. After such soaking, the pericarp is manually cut or picked off. Water soaking is not as effective as chemicals at loosening the pericarp.

To accurately identify parental lineage, a high yield of DNA is required for molecular analysis such as genome-wide genetic analysis. To obtain sufficient DNA for one sample using prior art methods, multiple seeds (usually on the order of 10 to 100 or so) have been needed. Manual removal of the pericarp from a sufficient number of individual seeds can take one, two, or more person-hours. Furthermore, it has been difficult, if not impossible, to completely remove all interior seed tissue, such as endospermic tissue, from the pericarp with the water soaking method, which makes it difficult to achieve the purity level needed or desired for accurate molecular analysis. In addition, the pooled DNA from multiple seeds, particularly from commercial seeds, brings a potential risk of contamination due to the mixing of seed source. To avoid such contamination and reduce the labor force, using a single seed for one sample would be desirable for molecular analysis.

There is a need for an improvement in the art of pericarp removal and tissue purification for accurate molecular analysis of pericarp tissue. Moreover, there is a need for the pericarp tissue sample to comprise tissue from fewer seeds, or even a single seed.

SUMMARY OF THE INVENTION

In this application the pericarp may be isolated such that it is free of other seed tissue, e.g., endosperm and embryo tissue, to obtain pure maternal DNA. Paternal lineage analysis may be derived from the maternal genotype in combination with the seed/embryo genotype.

One embodiment of the invention allows for determining the maternal lineage of one or more seeds by collecting maternal seed tissue from the one or more seeds; washing the maternal seed tissue; dissociating and homogenizing the maternal seed tissue to obtain a homogenized solution; centrifuging the homogenized solution to obtain supernatant; and performing a molecular analysis using supernatant DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociating and breaking pericarp tissue may be performed using a cell dissociator (such as gentleMACS™, Miltenyi Biotech). The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; dissociating and homogenizing the maternal seed tissue to obtain a homogenized solution; extracting DNA from cells contained within the homogenized solution; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The dissociating and homogenizing step may be performed using a cell dissociator (such as gentleMACS™, Miltenyi Biotech). The extracting step may be performed using DNA-binding magnetic particles or Extract-N-Amp™. The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; disrupting the maternal seed tissue in liquid nitrogen; extracting DNA from the disrupted maternal seed tissue; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The extracting step may be performed using DNA-binding magnetic particles or Extract-N-Amp™. The method may further comprise using whole genome amplification prior to the molecular analysis to obtain sufficient DNA yield.

Another embodiment of the invention allows for determining the maternal lineage of one or more seeds by collecting maternal seed tissue from the one or more seeds; washing the maternal seed tissue; extracting DNA directly from the washed maternal seed tissue; and performing a molecular analysis of the extracted DNA. In one embodiment, the maternal seed tissue is pericarp. The washing step may be performed with 1% sodium dodecyl sulfate solution, water, ethanol, or mixtures thereof. The washing step is preferably performed with an aqueous solution of about 1% sodium dodecyl sulfate. The extracting step may be performed using Extract-N-Amp™. The method may further comprise using whole genome amplification prior to the molecular analysis to obtain sufficient DNA yield.

In any of the embodiments stated above, the molecular analysis may be genotyping. When maternal seed tissue from more than one seed replicate is collected, a consensus genotype may be obtained.

DESCRIPTIONS OF THE DRAWINGS

FIG. 1 depicts the steps involved in peeling of pericarp tissue.

Figure 2:
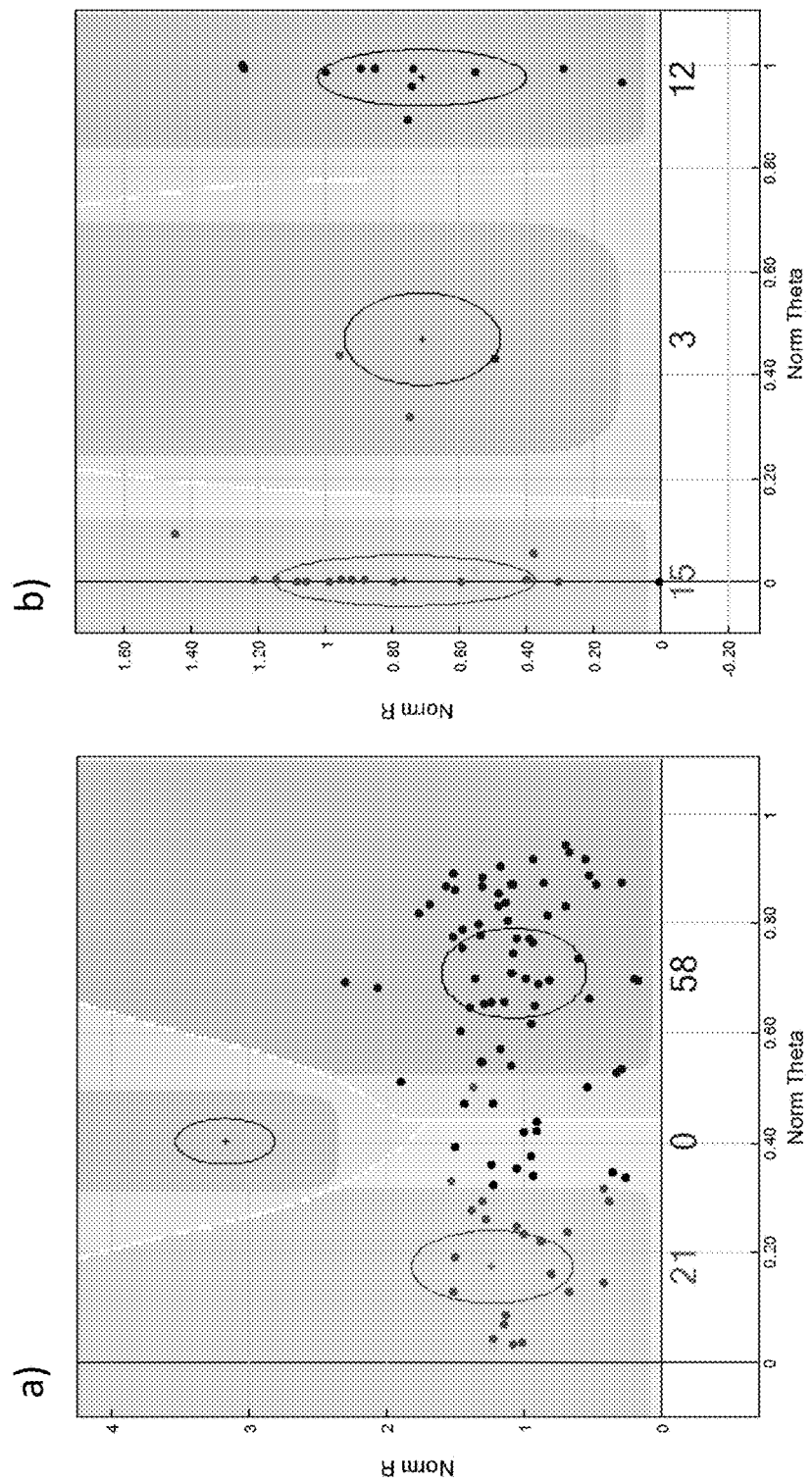

FIG. 2 compares the ILLUMINA® GOLDENGATE® Genotyping Assay using DNA obtained from a) conventional CTAB DNA extraction method using multiple seeds and b) SBEADEX® DNA extraction method using one seed (with tissue wash) followed by the whole genome amplification.

Figure 3:
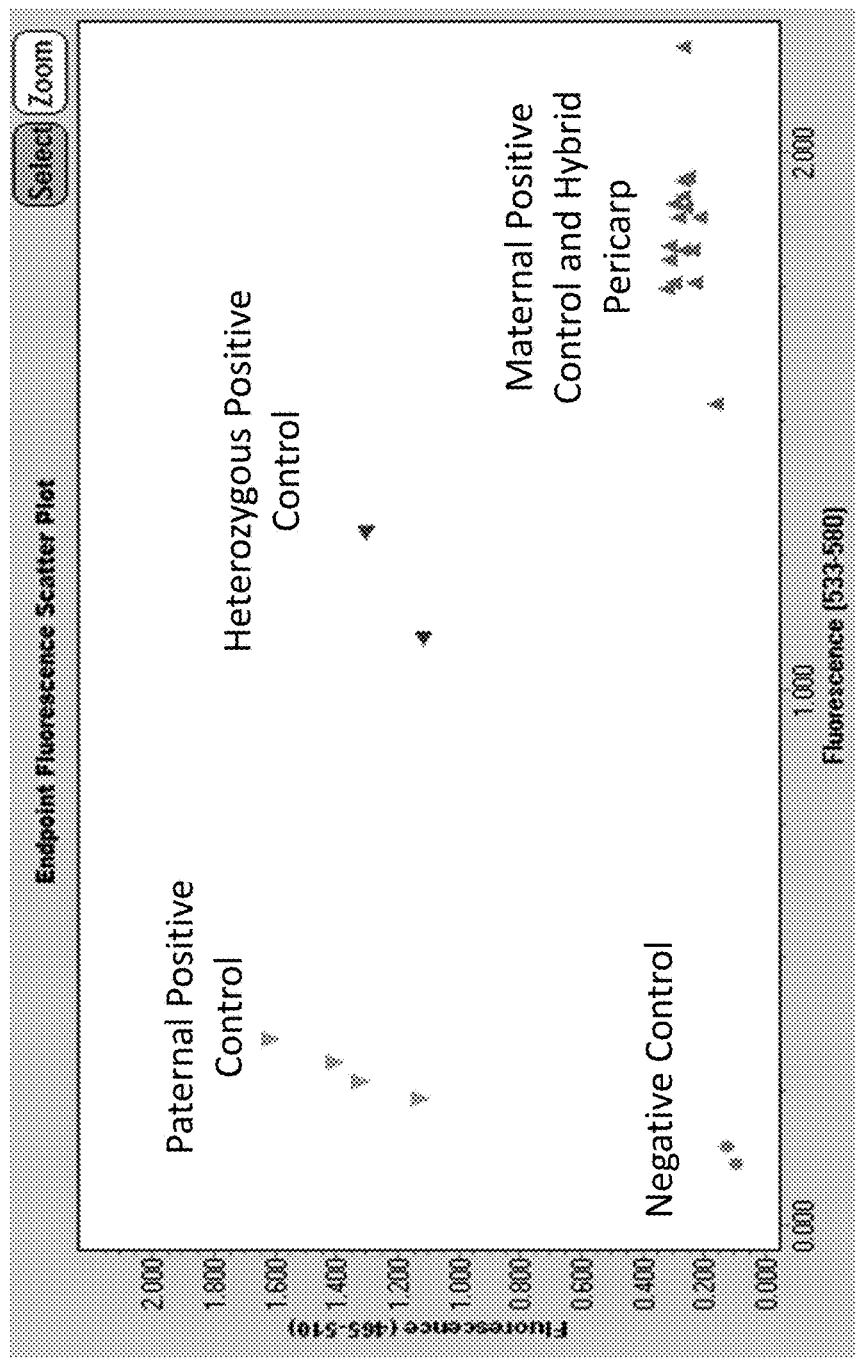

FIG. 3 demonstrates that quality fluorescent marker data can be obtained from a single pericarp.

Figure 4:
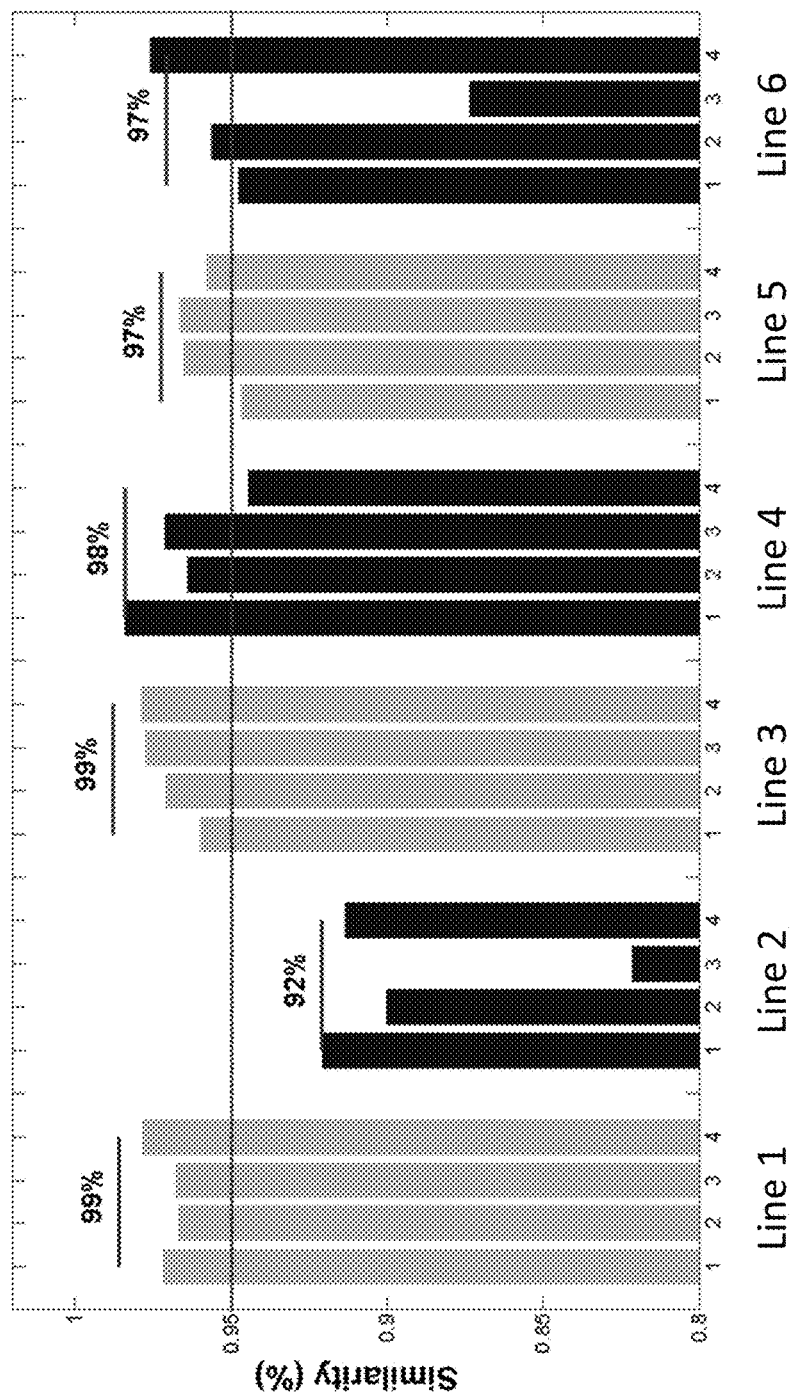

FIG. 4 demonstrates the high degree of similarity between the measured genotype of the pericarp tissue extracted from a single seed (each line) and the known maternal genotype.

DETAILED DESCRIPTION OF PREFERRED EMBODIMENTS

A piece of the outer coat of a corn kernel, the pericarp, may be excised in order to conduct a molecular analysis of the parent plant. In this embodiment, kernels may be soaked in water before making cuts in the pericarp. The back side of the kernel (farthest from the embryo) may be cut with a sharp blade, as shown in FIG. 1a. Preferably, the blade is sterilized after the first cut before outer edge of the kernel may be cut with the sharp blade, starting from one end of the first cut, around the edge of the kernel, and down to the other end of the first cut, as shown in FIG. 1b. Sterilized forceps may be used to peel the pericarp tissue from the kernel as shown in FIG. 1c. While the cut can be made on the front side of the kernel (nearest the embryo), the cut is preferably made on the back side to reduce the possibility that the pericarp will be contaminated with endosperm tissue. To further reduce the possibility of contamination, the pericarp tissue may be washed after it is excised. The pericarp may be placed in the well of a container and the seed from which the pericarp was excised (or the embryo from that seed) may be placed in a corresponding well of a separate container. As will be understood by those of ordinary skill in the art, there are other comparable methods for isolating pericarp tissue, and in some embodiments of the invention, pericarp DNA may be extracted without pericarp removal.

The tissue to be analyzed may be associated or correlated with its corresponding viable plant source so that the corresponding viable plant source can be selected based on the results of the tissue analysis. In some embodiments, particularly where the tissue to be analyzed is pericarp for purposes of maternal lineage determination, no corresponding viable plant source is needed.

Obtaining Genetic Material for Molecular Characterization

In one embodiment, pericarp tissue is collected and washed; tissue is dissociated and homogenized using gentleMACS™ from Miltenyi Biotech (or any other method known to one or ordinary skill in the art for the same purpose); and the homogenized solution is centrifuged. It was found that the resulting supernatant contained most of the DNA, as compared to the pellet, and thus, the DNA may be used directly in molecular analysis or to perform whole genome amplification followed by molecular analysis.

In another embodiment, pericarp tissue is collected and washed; tissue is dissociated and homogenized using gentleMACS™ from Miltenyi Biotech (or any other method known to one or ordinary skill in the art for the same purpose); DNA is extracted from cells contained within the homogenized solution using DNA extraction methods (such as but not limited to the SBEADEX® or the Extract-N-Amp™ methods); and the DNA may be used directly in molecular analysis or to perform whole genome amplification followed by molecular analysis.

In another embodiment, pericarp tissue is collected and washed; tissue is disrupted in liquid nitrogen; DNA is extracted using DNA extraction methods (such as but not limited to the SBEADEX® or the Extract-N-Amp™ methods); and the DNA may be used directly in molecular analysis or to perform whole genome amplification followed by molecular analysis.

In another embodiment, pericarp tissue is collected and washed; DNA is extracted directly from washed tissue using the Extract-N-Amp™ method (or any other method known to one or ordinary skill in the art for the same purpose); and the DNA may be used directly in molecular analysis or to perform whole genome amplification followed by molecular analysis.

Washing of the pericarp tissue reduces potential contamination from endospermic tissue. In any of the embodiments above, washing may be performed with aqueous 1% sodium dodecyl sulfate solution, water, ethanol, or mixtures thereof.

In any of the embodiments above, any method of DNA extraction known to those in the art may be used. For example, as stated previously, the SBEADEX® (magnetic particles that bind genetic material, which are available from LGC Genomics) or Extract-N-Amp™ methods may be used. In another example, genetic material may be extracted from tissue using an enzymatic DNA extraction method available from Sigma-Aldrich Enzymatic called Viscozyme L (See Sigma Aldrich product catalog).

Molecularly Characterizing the Genetic Material from the Pericarp

Whole genome amplification is a method for robust amplification of an entire genome, starting with nanogram quantities of DNA and resulting in microgram quantities of amplified products. Whole genome amplification has become an invaluable method for preserving limited samples of precious stock material, particularly when using whole genome amplification methods that have been developed to amplify material from a single cell. In some embodiments described herein, whole genome amplification may be performed prior to molecular analysis to obtain sufficient yield of DNA.

Any method known to one of ordinary skill in the art may be used to molecularly characterize the genetic material from the pericarp. Examples include but are not limited to the Qiagen REPLI-g and Sigma-Aldrich SeqPlex kits.

Other useful molecular characterizations may involve sequencing all or part of the genome of the pericarp extracted from the seed, or using molecular markers and fluorescent probes to genotype. Molecular analysis need not focus on the genotype of the extracted tissue, but instead may measure other properties such as: the epigenomic profile, the proteomic profile, the metabolic profile, oil content, oil composition, or the presence or absence of particular molecules in the tissue.

In one embodiment, a consensus genotype may be derived for the maternal line by considering genotypic data from pericarp tissue from multiple seeds (or multiple extractions of tissue from the same seed or seeds), each individual tissue specimen being a replicate. In a genotyping experiment that identifies multiple nucleotides across multiple positions in a genome, it is not uncommon for any particular experiment to fail to identify one or more of the nucleotides to be identified. Thus, missing or false nucleotide identifications for each position may be noted for each of the specimens. If nucleotide identification from only one specimen is available for a particular nucleotide position, then that nucleotide identification is assigned as the consensus data for that position. If two or more nucleotide identifications are available for a particular nucleotide position, then the majority nucleotide identity for that position is assigned as the consensus data for that position. If no majority identification exists for a position, that position is assigned as missing data for the consensus genotype. The probabilities for consensus accuracy for a given nucleotide position is given in Table 1 for the cases of 1, 2, 3, and 4 replicates, where f represents the average genotyping error rate.

TABLE 1

Probabilities of Consensus Accuracy

| Available Replicates | Consensus Call | Different Call | Probability |
|---|---|---|---|
| 1 | 1 | 0 | $1 - f$ |
| 2 | 2 | 0 | $1 - f^2$ |
| 2 | 1 | 1 | 0.5 |
| 3 | 3 | 0 | $1 - f^3$ |
| 3 | 2 | 1 | $1 - 3 * (1 - f) * f^2$ |
| 4 | 4 | 0 | $1 - f^4$ |
| 4 | 3 | 1 | $1 - 4 * (1 - f) * f^3$ |
| 4 | 2 | 2 | 0.5 |

While the examples provided here relate to obtaining and genotyping pericarp tissues from a monocot, specifically maize, those of ordinary skill in the art would understand how to apply the same or similar methods to maternal seed tissue from other monocots and dicots. The methods may be adapted to any plant whose seed includes maternal tissue. For instance, the plant may be selected from the group consisting of: maize, soybean, sunflower, sorghum, canola, wheat, alfalfa, cotton, rice, barley, millet, sugar cane and switchgrass. Further, the genotyping methods disclosed herein may be used to genotype any plant tissue. The consensus genotyping methods may also be used to generate a consensus genotype for multiple samples of any genetic material obtained from any source without departing from the steps disclosed.

Example: Pericarp Genotyping

A. Pericarp Peeling

Kernels of corn were removed from the cob and soaked for 60 minutes in deionized water. A scalpel blade was sterilized using a bead sterilizer. The scalpel was used to cut the back side of the seeds (away from the embryo) near the tips, as shown in FIG. 1a. The scalpel was again sterilized using a bead sterilizer and cooled in sterile water. The scalpel was then used to cut along the outer edge of the kernel, as shown in FIG. 1b. Forceps were sterilized in a bead sterilizer, cooled, then used to peel the pericarp from the kernel, as shown in FIG. 1c. The pericarp tissue from each kernel was then placed in microcentrifuge tubes.

B. Pericarp Washing

Three different washing solutions were tested. The best results were achieved washing with 1% sodium dodecyl sulfate (SDS) solution, although adequate results were achievable using water and ethanol. An alternative washing method using sonication also gave adequate results. The washing protocol used began by adding 1 mL wash solution to the microcentrifuge tubes, which was placed in an inverter for 1 minute. The wash solution was removed and replaced with 1 mL fresh wash solution, then the microcentrifuge tubes were again placed in an inverter, this time for 4 minutes. The pericarp tissue was then removed, rinsed with distilled water, and placed into a new microcentrifuge tube. The sonication protocol placed the pericarp tissue in a sonicator for 1 minute. The tissue was then removed, rinsed with distilled water, and placed in a fresh microcentrifuge tube.

C. Obtaining DNA

Five methods for obtaining DNA were tested. The best results were achieved with the gentleMACS™ protocol with water or TE supernatants.

gentleMACS™/Water or TE supernatants: In this method, pericarp tissue was placed directly onto the rotor of a gentleMACS™ M tube. 300 ul of water or TE buffer was added to the tube, which was then closed and placed in a gentleMACS™ machine. The automated program "Protein_01.01" was run. For pericarp tissues that were not fully dissociated, further mixing and running of the automated program was done. Next, the mixtures were spun down in the GentleMACS™ tube and transferred to a new 1.5 ml Eppendorf tube. The Eppendorf tube was then centrifuged at 14000 rpm for 2 minutes, and the supernatant were transferred to a fresh 1.5 ml Eppendorf tube for the molecular analysis. No extraction of DNA was required in this method.

GentleMACS™/SBEADEX® In this method, pericarp tissue was placed directly onto the rotor of a gentleMACS™ M tube. 300 μL of SBEADEX® Lysis Buffer PN was added to the tube, which was then closed and placed in a gentleMACS™ machine. The automated program "Protein_01.01" was run. For pericarp tissues that were not fully dissociated, further mixing and running of the automated program was done. Next, the mixtures were centrifuged and incubated at 65° C. for 1 hour with occasional agitation. 360 μL of Binding Buffer PN and 30 μL SBEADEX® particles were added to fresh 1.5 mL Eppendorf tubes. The tubes with the pericarp tissue were centrifuged and the lysate was transferred to the fresh tubes. These were then incubated at room temperature for 4 minutes to allow the DNA to bind to the SBEADEX® particles. The tubes were then vortexed briefly then placed in a magnetic rack to concentrate the beads. The lysis buffer was removed and 600 μL of wash buffer PN1 was added to each tube and the beads were resuspended. The tubes were again placed in a magnetic rack to concentrate the beads and the wash buffer PN1 was removed. This washing procedure was repeated using 600 μL of wash buffer PN2, then repeated again using 600 μL of pure water. Following this third washing step, 40 μL of elution buffer PN was added and the tubes were incubated at 55° C. for 20 minutes and vortexed every 3 minutes. A magnetic plate was used to concentrate the beads, and the eluate was transferred into fresh tubes, then stored at −20° C. until molecular characterization.

gentleMACS™/Extract-N-Amp™: In this method, pericarp tissue was again placed directly onto the rotor of a gentleMACS™ M tube. 300 µL of sterile water was added to the tube, which was then closed and placed in a gentleMACS™ machine. The automated program "Protein_01.01" was run. For pericarp tissues that were not fully dissociated, further mixing and running of the automated program was done. The homogenate was transferred to a 1.5 mL microcentrifuge tube and centrifuged for 1 minute at 10,000 rpm. The supernatant was removed without disturbing the tissue pellet at the bottom of the tube. 30 µL of Extraction Solution/Seed Preparation Solution mix (Sigma-Aldrich Extract-N-Amp™ Seed PCR kit) was added and the resulting mixture was thoroughly mixed. The mixture was transferred to PCR strip tubes for use on the thermocycler, which was programmed to hold 55° C. for 10 minutes, then 95° C. for 3 minutes, then to hold 4° C. indefinitely. 30 µL of Neutralization Solution B was added.

Liquid Nitrogen/SBEADEX®:

1.5 mL microcentrifuge tube pestles were placed in liquid nitrogen to cool. Pericarp tissue was placed in microcentrifuge tubes along with the cooled pestles and the entire tube was placed in liquid nitrogen. Liquid nitrogen was added to the tubes. The pericarp tissue was ground slowly and thoroughly using the pestle. The tubes were occasionally dipped back into the liquid nitrogen to keep the tissue cold. After grinding, 90 µL of Lysis buffer PN was added to each tube, which was then briefly centrifuged then incubated at 65° C. for 1 hour. 120 µL of binding buffer PN and 10 µL of SBEADEX® particles were added to fresh tubes, and the lysate from the grinding step was added to the new tubes. These were then incubated at room temperature for 4 minutes to allow the DNA to bind to the SBEADEX® particles. The mixtures were then briefly vortexed and placed in a magnetic rack to concentrate the beads. The lysis buffer was removed and 200 µL of wash buffer PN1 was added to each tube and the beads were resuspended. The tubes were again placed in a magnetic rack to concentrate the beads and the wash buffer PN1 was removed. This washing procedure was repeated using 200 µL of wash buffer PN2, then repeated again using 200 µL of pure water. Following this third washing step, 20 µL of elution buffer PN was added and the tubes were incubated at 55° C. for 10 minutes and vortexed every 3 minutes. A magnetic plate was used to concentrate the beads, and the eluate was transferred into fresh tubes, then stored at −20° C. until molecular characterization.

Extract-N-Amp™:

A master mix of 18 parts extraction solution and 2 parts of seed preparation solution was made and 20 µL of the solution added to pericarp tissue in 0.2 mL PCR strip tubes. The mixtures were placed in a thermocycler set at 55° C. for 10 minutes, 95° C. for 3 minutes, then 4° C. indefinitely. 20.0 µL of Neutralization Solution B was added and the liquid portion of the mixture was transferred to fresh 1.5 mL microcentrifuge tubes.

D. Molecular Testing

QUBIT® dsDNA HS Assay Kit:

QUBIT® reagent was diluted into QUBIT® buffer at a 1:200 ratio to make a working solution. 1 µL of the PCR products of step 2B was transferred to 0.5 mL QUBIT® assay tubes and 199 µL of the working solution. Standards were made by adding 10 µL of standard to 190 µL of QUBIT® working solution. The PCR products and standards were vortexed for 2-3 seconds then briefly centrifuged. The tubes were then incubated at room temperature for 2 minutes. The tubes were then inserted into a QUBIT® 2.0 fluorometer and readings were recorded.

Whole Genome Amplification (Seqplex):

The preferred method of whole genome amplification is the Seqplex method using the Seqplex Enhanced DNA Amplification Kit. To 1 µL of each DNA solution generated in step C was added 2 µL library preparation buffer and 11 µL pure water. The solution was centrifuged, vortexed, and centrifuged again, incubated on a thermocycler at 95° C. for 2 minutes, then held at 4° C. After cooling, 1 µL of library preparation enzyme was added. The solution was centrifuged, vortexed, and centrifuged again, then incubated on a thermocycler at 16° C. for 20 minutes, 24° C. for 20 minutes, 37° C. for 20 minutes, 75° C. for 5 minutes, then held at 4° C. The solution was the briefly centrifuged. 15 µL of this solution was added to 15 µL of 5× Amplification Mix (A5112), 1.5 µL DNA Polymerase for SeqPlex (SP300), 42.5 µL sterile water (W4502) and 1 µL SYBR Green (S9403), diluted 1:1000. This solution was mixed thoroughly, and each reaction mix was divided into five 15 µL aliquots on a 384 well plate. The amplification thermocycle began with an initial denaturation at 94° C. for 2 minutes followed a sufficient number of cycles to reach 2-3 cycles into the plateau (typically about 24 cycles): 94° C. denature for 15 seconds, 70° C. anneal/extend for 5 minutes, read fluorescence, repeat. After cycling, the reaction mix was held at 70° C. for 30 minutes then held at 4° C. After cooling, the samples were purified via QIAquick PCR purification.

Whole Genome Amplification (REPLI-g Single Cell Kit):

Denaturation buffer D1 was prepared by adding 3.5 µL of reconstituted buffer DLB and 12.5 nuclease-free water. Neutralization buffer N1 was prepared by adding 4.5 µL of stop solution and 25.5 µL of nuclease-free water. 2.5 µL of the denaturation buffer was added to each 2.5 µL aliquot of DNA solution prepared in step C. This solution was incubated at room temperature for 3 minutes. 5.0 µL of the neutralization buffer N1 was added, and the solution was vortexed then centrifuged briefly. Master mix was prepared with 9.0 µL nuclease-free water, 29.0 µL of REPLI-g reaction buffer, and 2.0 µL of REPLI-g DNA polymerase per reaction. 40.0 µL of this master mix was added to each solution, which is then run on a thermocycler at 30° C. for 8 hours, then cooled to 4° C.

The whole genome amplification products were evaluated using the QUBIT® assay to determine yield of DNA.

Genotyping Assays.

Both high density markers (the ILLUMINA® 3072X chip) and Taqman marker analysis were successfully employed to genotype the genetic materials described in this example. Data demonstrating the effectiveness of the foregoing techniques is presented in FIGS. 2-4. FIG. 2 compares the data quality obtained using DNA extraction methods against that obtained using whole genome amplification. While both methods give acceptable results, the whole genome amplification method gives preferable results, with each of the three haplotypes well-resolved. FIG. 3 is a fluorescent marker scatter plot demonstrating that quality fluorescent marker data can be obtained from a single pericarp tissue sample. In fact, the methods of the invention allow genotyping using many markers, tens or potentially hundreds, using pericarp tissue extracted from a single seed. FIG. 4 demonstrates the reliability of the methods of the invention because of the high degree of similarity between the measured genotype of the pericarp tissue extracted from a single seed (each line) and the known maternal genotype.

We claim:

1. A method for determining the maternal genotype of a single hybrid maize seed comprising:
   (a) collecting pericarp tissue from a sample consisting of the single hybrid maize seed;
   (b) washing the pericarp tissue from the sample consisting of the single hybrid maize seed with an aqueous 1% sodium dodecyl sulfate (SDS) solution;
   (c) dissociating and homogenizing the pericarp tissue from the sample consisting of the single hybrid maize seed using a cell dissociator to obtain a homogenized solution;
   (d) centrifuging the homogenized solution obtained in step (c) to obtain supernatant; and
   (e) genotyping DNA contained within the supernatant, wherein a genotype obtained is a single maternal genotype of the pericarp tissue from the sample consisting of the single hybrid maize seed, and wherein the single hybrid maize seed pericarp genotype is obtained without performing a DNA extraction step.

2. The method of claim 1, wherein whole genome amplification is performed prior to genotyping.

3. The method of claim 2, further comprising genotyping the single hybrid maize seed and comparing the genotype of the pericarp tissue from the sample consisting of the single hybrid maize seed and the genotype of the single hybrid maize seed to obtain paternal lineage.

\* \* \* \* \*